United States Patent [19]

Aronsohn

[11] Patent Number: 4,774,935
[45] Date of Patent: Oct. 4, 1988

[54] POST SURGERY DEVICE

[76] Inventor: Richard B. Aronsohn, 6333 Wilshire Blvd., Los Angeles, Calif. 90048

[21] Appl. No.: 944,174

[22] Filed: Dec. 22, 1986

[51] Int. Cl.[4] .......................... A61F 13/12; A61F 5/28
[52] U.S. Cl. .................................. 128/76 B; 128/97.1
[58] Field of Search ........................ 128/76 B, 380, 97

[56] References Cited

U.S. PATENT DOCUMENTS

| | | | |
|---|---|---|---|
| 922,420 | 5/1909 | Hannig | 128/76 B |
| 971,373 | 9/1910 | Hannig | 128/76 B |
| 1,439,910 | 12/1922 | Posa | 128/76 B |
| 2,504,791 | 4/1950 | Baron | 128/76 B |
| 2,565,123 | 8/1951 | DeMar | 128/76 B |
| 4,658,811 | 4/1987 | Beaird | 128/76 B |

FOREIGN PATENT DOCUMENTS

| | | | |
|---|---|---|---|
| 8988 | 8/1908 | France | 128/76 B |
| 238829 | 8/1925 | United Kingdom | 128/76 B |

Primary Examiner—Clyde I. Coughenour
Attorney, Agent, or Firm—Bogucki, Scherlacher, Mok & Roth

[57] ABSTRACT

A post surgery device and method includes a pair of pressure pads and a harness that extends around the back of a patient's head to retain the pressure pads against the naso-labial region of the patient's face following a lipo-suction procedure to reduce naso-labial folds. A metal wire extends past the nose of the patient between the pair of pressure pads to complete a peripheral force loop to maintain sufficient inward force upon the pressure pads to compress the skin tissue against the subdermal muscle tissue to inhibit separation and swelling while healing proceeds. For a typical patient, the device is worn continuously for about two days following surgery and then for about four days thereafter with occasional interruptions being permitted.

11 Claims, 2 Drawing Sheets

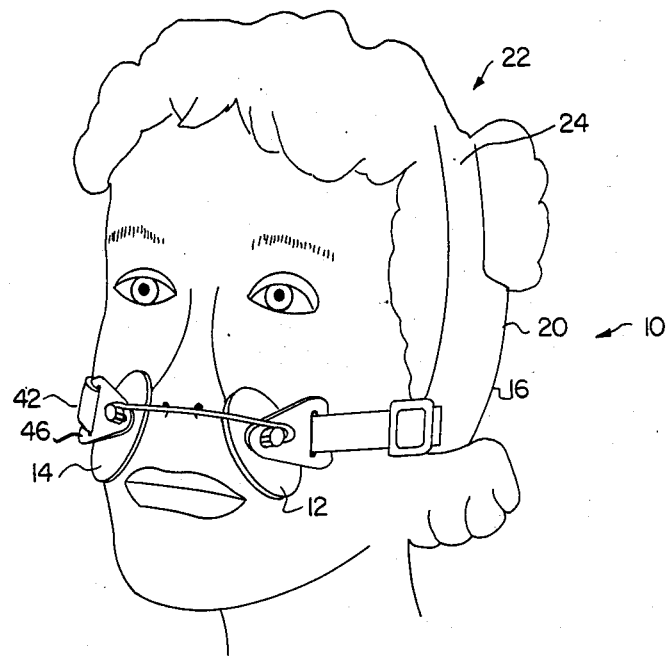
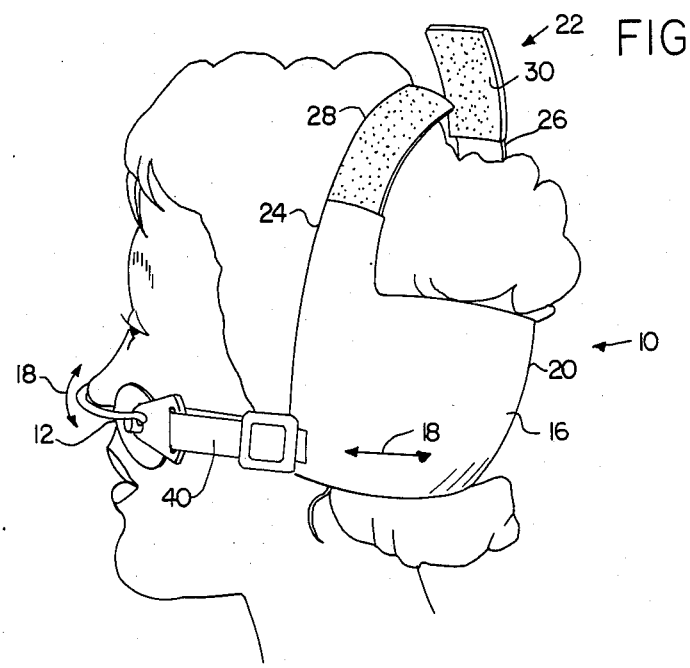

POST SURGERY DEVICE

BACKGROUND OF THE INVENTION

As a person ages and acquires body fat, it is common to experience a formation of naso-labial folds that run from the ala of the nose to the corner of the mouth on the same side of the face. As discussed in an article, Richard B. Aronsohn, M.D., "Lipo-Suction of the Naso-labial Fold: A preliminary Report", *The American Journal of Cosmetic Surgery*, Vol. 1, No. 2 (Spring 1984), a lipo-suction technique is now available to correct naso-labial folds.

The lipo-suction naso-labial fold reduction technique involves insertion of a cannula beneath the skin to suck out a small amount of fat in the region of a fold. The procedure creates a tunneling or honeycomb effect and eliminates many of the fibrous attachments of the skin to the muscles beneath the skin. While a small compressible sponge may initially be placed over the suctioned area and secured by elastoplast tape, a fold may tend to sag under the effect of gravity as healing proceeds. In addition, there may be some bruising and swelling in the suctioned area as a result of the procedure.

SUMMARY OF THE INVENTION

A method of reducing naso-labial folds in accordance with the invention includes lipo-suction of the subdermal fold region followed by compression and support of each fold region by a head supported naso-labial fold compression device having a pair of fold engaging pressure pads. Each pressure pad has a generally flat skin engaging surface that is contoured for mating engagement with a fold region and a generally circular perimeter.

The pressure pads are resiliently supported in compressive relationship to the nasal labial fold regions of a patient's face by a harness. The harness provides a force loop which encircles the wearer's head at the height of the naso-labial folds and includes a front piece which extends across the face of the wearer between the two pressure pads. A posterior web member band extends behind the head to left and right adjustable, elastic straps having a rearward end affixed to the band and a triangular shaped connector extending between a pressure pad and a front end of the strap. The posterior web member forms a relatively wide band which extends behind the head and forward to approximately the front portion of each ear. It includes an adjustable top strap that extends over the top of the head to vertically locate the web member band.

The compression device is worn continuously for about two days during an initial healing period following a lipo-suction procedure, and thereafter may be occasionally removed over an additional four day period. An inward and upward force exerted by the pressure pads tends to prevent gravitationally induced sagging of the fold area skin, compress the honeycombed subdermal fat tissue and hold the skin against the underlying muscles as the fibrous connective tissue is reestablished following the lipo-suction procedure.

BRIEF DESCRIPTION OF THE DRAWINGS

A better understanding of the invention may be had from a consideration of the following Detailed Description taken in conjunction with the accompanying drawings in which:

FIG. 1 is a front perspective view of a post surgical compression device in accordance with the invention;

FIG. 2 is a perspective side view of the compression device shown in FIG. 1.

DETAILED DESCRIPTION

Figure 3:
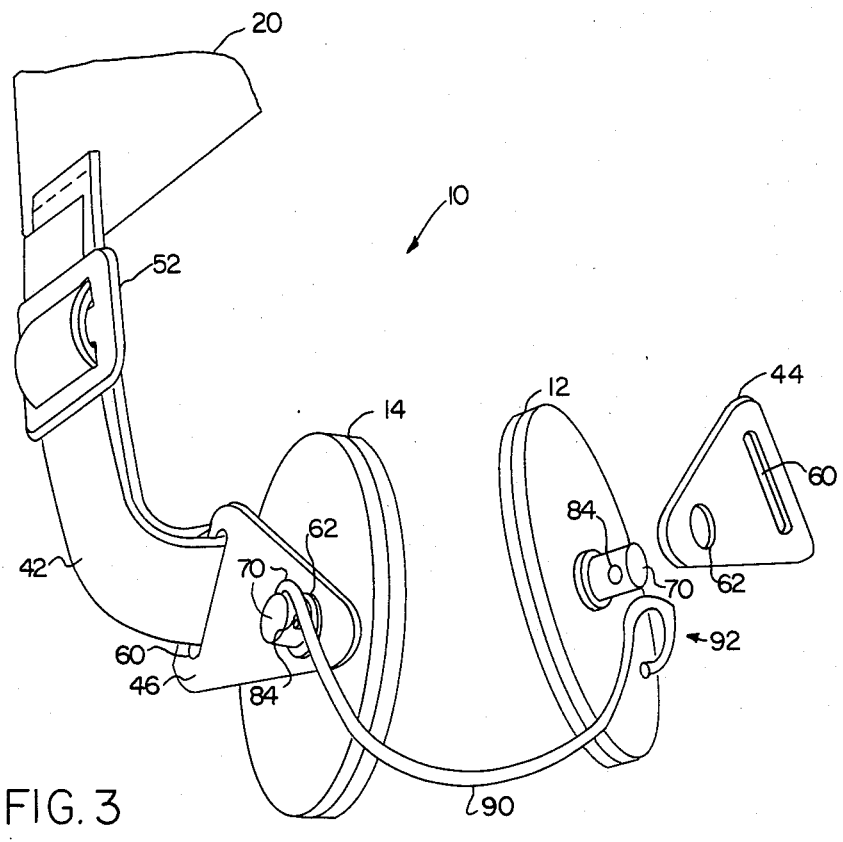
FIG. 3 is an enlarged fragmentary view of a portion of the compression device shown in FIG. 1.

Referring now to FIGS. 1-3, a post surgical compression device 10 in accordance with the invention is worn by a patient following surgical reduction of naso-labial folds to prevent separation of adjacent skin tissue from subdermal muscle tissue and to control swelling. The compression device 10 includes left and right pressure pads 12, 14, which are forced inwardly toward the face in the region of the naso-labial folds, as well as a harness 16 which secures the pressure pads 12, 14 to the face and exerts sufficient inward force upon the pads 12, 14 to assure that the skin tissue in the vicinity of the naso-labial folds does not separate from the subdermal muscle tissue while healing proceeds following a surgical reduction procedure.

The harness 16 provides a force perimeter or tension loop 18 about the head in the vicinity of the naso-labial folds. The tension loop 18 provides the radially inward directed force normal to the surgical region of the patient's face which compresses the pressure pads against the face. The harness 16 includes a posterior web member 20 which is preferably made of a soft, flexible fabric and forms a relatively wide head band that extends from approximately the front of each ear around the back of the head along a lower portion thereof.

A top strap 22 has left and right side straps 24, 26 which extend over the top of the head to secure the band 20 at a suitable up and down position on the head. The straps 24, 26 are adjustably connectable to each other at their outer ends by suitable means such as Velcro wool 28 and hooks 30. The straps 24, 26 are secured to the band 20 at the top front portion thereof on the left and right sides respectively just above the ears.

Left and right elastic straps 40, 42 are secured by stitching to the head band 20 on left and right sides thereof at lower front positions. They extend forwardly to form a loop through left and right triangular shaped strap connectors 44, 46 with the ends being looped back to be adjustably secured by left and right buckles 50, 52.

The triangular connectors 44, 46 are identical and are planar members which may be made of plastic and have a slot 60 extending along one edge which receives a strap 40 or 42 therethrough. A circular aperture 62 is positioned adjacent a vertex opposite the slot 60 and receives a post 70 to secure the connector to one of the pressure pad 12, 14.

Figure 4:
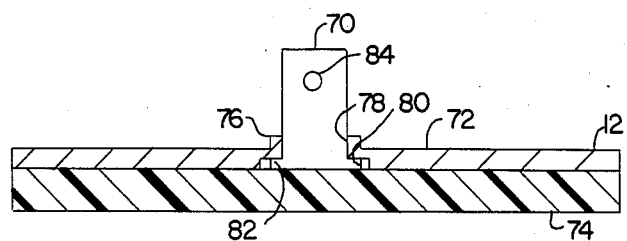
FIG. 4 is a sectional elevational view of a compression pad used in the compression device shown in FIG. 1.

The pressure pads 12, 14 may be identical and are represented by the pad 12 which is shown in greater detail in FIG. 4, to which further reference is now made. The pressure plate includes a planar, disk-shaped support plate 72 which may be made of a suitably strong plasstic and a disk-shaped pad 74 which may be made of a resilient padding material such as foam rubber in addition to the post 70. The pad 74 is bonded by adhesive or other suitable means to a facial side of the support plate 72.

The support plate has a central boss 76 which provides added strength in the vicinity of a central bore 78 and counterbore 80 which receive the generally cylindrical post 70. Post 70 has a flange 82 which is matingly received by the counterbore 80 to restrain the post 70 between the support plate 72 and pad 74. No adhesive is applied between the pad 74 and support plate 72 in the vicinity of counterbore 80 and flange 82 so that post 70 is free to rotate within central bore 78.

A transverse bore 84 is drilled through post 70 adjacent an outer end thereof to receive a front piece 90. The front piece 90 is made of a relatively strong wire such as No. 10 steel wire and is preferably tempered to help it retain its initial shape.

The front piece 90 extends across the front of the face in the oral nasal region thereof slightly below the nose and between the pressure pads 12, 14 to complete a perimeter of force about the wearer's head. As most clearly seen in Fig. 3, each end of the front piece passes rearwardly over the top of a post 70 of a pressure pad 12 or 14 and is then bent to pass in a forward direction through a bore 84. The ends may be closed against the front piece 90 so as to form closed end loops 92 passing through the bores 84 to assure that front piece 90 remains attached to the posts 70 of pressure pads 12, 14. The triangular connectors 44, 46 are assembled to the posts 70 before the front piece 90 is attached and are thus constrained between the end loops 94 of front piece 90 and the support plate 72.

After the lipo-suction technique or similar surgical procedure has been completed the compression device 10 is placed on the head of the patient by slipping the harness 16 over the patient's head and adjusting the top strap 22 to secure the harness in place at the proper level. The pressure pads are located at the vicinity of the naso-labial folds and the straps 40, 42 are adjusted to provide a proper inwardly directed force upon the pressure pads 12, 14. This force should be sufficient to help prevent swelling and to maintain the affected skin area in contact with the subdermal muscle tissue without imposing unnecessary discomfort on the patient. The compression device 10 is attached by the surgeon or surgical staff and continuously left in place, typically for two days. Thereafter the patient may occasionally remove and replace the device 10 until the surgical area has healed sufficiently that the compressive force is no longer required to prevent swelling or separation of the skin from the underlying tissue. Four additional days are typically sufficient for this to occur.

While there has been shown and described above a particular embodiment of a surgical compressor device in accordance with the invention for the purpose of enabling a person of ordinary skill in the art to make and use the invention, it should be appreciated that the invention is not limited thereto. Accordingly, any modifications, variations or equivalent arrangements within the scope of the annexed claims should be considered to be within the scope of the invention.

What is claimed is:

1. A compression device for shaping a naso-labial area of a human patient following reduction of a naso-labial fold in the naso-labial area by lipo-suction, the compression device comprising:

a pressure pad disposed to press against the naso-labial area in a direction generally perpendicular to a surface thereof with sufficient force to overcome effects of gravity and of swelling in the naso-labial area to preserve a generally flat shape on the surface thereof; and a complete peripheral resilient loop passing around the head of the patient past the naso-labial area and around the back of the head without touching the nose, the loop including a wire passing from the pressure pad that is curved to extend around the oral-nasal region of the face spaced-apart therefrom and the loop being coupled to the pressure pad and imparting the sufficient force thereto.

2. A compression device according to claim 1, wherein the wire is a steel wire that is tempered to retain its initial shape.

3. A compression device according to claim 1, wherein the loop includes a web portion extending from the region of each ear rearwardly around and behind the head of the patient, the web portion being sufficiently wide to cover the ears of the patient.

4. A compression device for shaping a pair of naso-labial areas of a patient following reduction of folds in the naso-labial areas by lipo-suction, the compression device comprising:

a pair of pressure pads disposed to press against the respective ones of the pair of nasal labial areas in a direction generally perpendicular to a surface thereof with sufficient force to overcome effects of gravity and of swelling in the naso-labial area to preserve a desired contour shape on the surface thereof; and a harness providing a complete peripheral loop passing around the head of the patient past the naso-labial areas and around the back of the head, the loop including a wire extending between the pressure pads and curving past the oral-nasal region of the face spaced apart therefrom and the loop being coupled to the pressure pads at a central region thereof and imparting the sufficient force thereto.

5. A compression device according to claim 4 wherein the pressure pads each have a disc-shaped configuration with a post extending from the central region thereof, the post being secured to the harness.

6. A compression device according to claim 5 wherein a compressive force is transmitted from the harness through the posts to the pressure pads to hold the pressure pads firmly against the naso-labial areas of the face of the patient.

7. A compression device for compressing a naso-labial area of a patient's face following a surgical procedure, the compression device comprising:

first and second disc-shaped pressure pads adapted to bear against naso-labial regions of the patient's face, each having a centrally located post extending therefrom; and a harness adapted to be secured to the head of the patient and connected to the posts of the first and second pressure pads to exert a force thereon directed toward the naso-labial area of the face of the patient, the harness including a head band extending from at least the front edge of each ear and behind the head with sufficient width to encompass each ear in a vertical direction, the band being coupled at each end to the central post of a different one of the first and second pads, the harness further including a front piece extending across the face of the patient spaced apart from the oral-nasal region of the face and secured to the posts of the first and second pads to position the pads and complete a peripheral loop about the head of the patient and secure the harness to the posts.

8. A compression device according to claim 7 wherein the harness further comprises an adjustable top strap that is connected to the head band at opposite ends thereof and is adapted to pass over the top of the head of the patient to secure the harness at a desired vertical position.

9. A compression device according to claim 7 wherein the harness further comprises a pair of adjustable straps coupling the opposite ends of the head band to the posts of the respectively left and right pressure pads.

10. A compression device according to claim 7 wherein the front piece comprises a wire having opposite ends looped through bores in the posts of left and right pressure pads respectively.

11. A compression device according to claim 7 wherein the first and second pressure pads each include a support plate having a planar surface oriented in facing relationship to the face of the patient and a central aperture receiving the post and a pad secured to the surface of the support plate which is oriented toward the face of patient.

* * * * *